(12) United States Patent
Sun et al.

(10) Patent No.: US 9,723,831 B2
(45) Date of Patent: Aug. 8, 2017

(54) SYSTEM AND METHODS FOR AUTOMATED VITRIFICATION OF BIOLOGICAL MATERIALS

(71) Applicant: The Governing Council of the University of Toronto, Toronto (CA)

(72) Inventors: Yu Sun, Toronto (CA); Jun Liu, Toronto (CA)

(*) Notice: Subject to any disclaimer, the term of this patent is extended or adjusted under 35 U.S.C. 154(b) by 319 days.

(21) Appl. No.: 14/447,245

(22) Filed: Jul. 30, 2014

(65) Prior Publication Data

US 2016/0029619 A1 Feb. 4, 2016

(51) Int. Cl.
*A01N 1/00* (2006.01)
*C12M 1/00* (2006.01)
*A01N 1/02* (2006.01)
*G02B 21/32* (2006.01)
*G02B 21/36* (2006.01)

(52) U.S. Cl.
CPC .......... *A01N 1/0252* (2013.01); *G02B 21/32* (2013.01); *G02B 21/365* (2013.01)

(58) Field of Classification Search
CPC ........ C12M 21/08; A01N 1/02; A01N 1/0236; A01N 1/0263; A01N 1/0268; A01N 1/0273
See application file for complete search history.

(56) References Cited

U.S. PATENT DOCUMENTS

| | | | |
|---|---|---|---|
| 2002/0009704 A1 | 1/2002 | Yang et al. | |
| 2002/0090320 A1* | 7/2002 | Burow | B01L 9/523 422/64 |
| 2008/0092581 A1* | 4/2008 | Schumann | A01N 1/02 62/378 |
| 2009/0144494 A1* | 6/2009 | Lin | A01N 1/0236 711/112 |
| 2009/0186405 A1 | 7/2009 | Chin | |
| 2011/0207112 A1 | 8/2011 | Burbank et al. | |
| 2012/0251999 A1 | 10/2012 | Demirci et al. | |
| 2012/0297797 A1* | 11/2012 | Cognard | A47J 41/024 62/51.1 |
| 2013/0137080 A1 | 5/2013 | Henderson et al. | |
| 2013/0157362 A1 | 6/2013 | Du et al. | |

FOREIGN PATENT DOCUMENTS

| | | |
|---|---|---|
| CN | 202918907 U | 5/2013 |
| WO | 2013020032 A2 | 2/2013 |
| WO | 2013098825 A1 | 7/2013 |

OTHER PUBLICATIONS

English machine translation of CN 102835389 (which is equivalent to CN 202918907), 2013.*

(Continued)

*Primary Examiner* — Nathan Bowers
(74) *Attorney, Agent, or Firm* — Eduardo Krupnik; Miller Thomsons LLP

(57) ABSTRACT

The present invention relaters to a system and methods for automated vitrification of mammalian oocytes or embryos. The system and methods enable automated processing of oocytes or embryos in vitrification solutions; robotically moving vitrification devices that carry processed cells for freezing in liquid nitrogen; automated sealing of the frozen devices; and transferring the sealed devices to an automated storage system for long-term cryopreservation.

25 Claims, 9 Drawing Sheets

(56) References Cited

OTHER PUBLICATIONS

Heo, Y. et al. Controlled Loading of Cryoprotectants (CPAs) to oocyte with linear and complex CPA profiles on a microfluidic platform, Lab on a Chip, 2011, p. 3530-3037, vol. 11 No. 20.
Lu, Zhe et al. Single Cell Deposition and patterning with a Robotic System, PLoS One, Oct. 2010, e13542, vol. 5 No. 10.
Origio Medicult Media, Medicult Vitrification Cooling Protocol, 2014.
Kitazato Inc., Cryotop Safety Kit: Vtirification Protocol for Cryotop Method, 2014.

* cited by examiner

SYSTEM AND METHODS FOR AUTOMATED VITRIFICATION OF BIOLOGICAL MATERIALS

FIELD OF THE INVENTION

The present invention relates generally to the field of detection, processing, and manipulation of biological cells, and in particular to systems and methods for vitrification of mammalian oocytes or embryos.

BACKGROUND OF THE INVENTION

Cryopreservation of mammalian reproductive cells is an essential technique in IVF (in vitro fertilization) clinics. Oocytes and embryos are routinely frozen and preserved for use at a later time. Patients who undergo therapeutic procedures that can place their fertility at risk, such as chemotherapy, have the option of preserving their oocytes for future use through IVF techniques. Additionally, fertilized embryos are often more needed for one cycle of IVF treatment. The rest of fertilized embryos are usually cryopreserved for future use.

Techniques of oocyte/embryo cryopreservation are classified into two categories, slow freezing and fast freezing (i.e., vitrification). Slow freezing is a well-established technique developed during the early 1970s, which makes use of programmable sequences, or controlled cooling rates. Vitrification or fast freezing is a more effective cryopreservation method, first reported in 1985 (see W. F. Rall and G. M. Fahy, "Ice-free cryopreservation of mouse embryos at −196 degrees C. by vitrification," Nature, vol. 313, no. 6003, pp. 573-5, 1985). Vitrification is considered superior to slow freezing, because it vitrifies the oocyte/embryo with no crystal formation during freezing. The addition of cryoprotectants in vitrification increases the embryo viscosity, and makes the vitrified embryos syrupy. When directly freezing oocytes/embryos in liquid nitrogen, the syrupy content inside the cell forms amorphous ice instead of ice crystals, which minimize the vital damage to the cell during freezing.

Oocyte/embryo vitrification is done manually in IVF clinics. An operator looks though the microscope eyepieces and manipulates oocytes/embryos using a micropipette. An oocyte/embryo is first taken out from the culture dish and washed with the equilibrium solution (ES) and a series of vitrification solution (VS). Within each step, the control of timing has been proven critical. After the washing steps, the processed oocyte/embryo is placed onto a vitrification straw or into a cryo-pipette. The volume of solution remained around the oocyte/embryo on the straw must be minimal in order to ensure a high cooling rate. The vitrification straw is then plunged into liquid nitrogen for freezing and long-term cryopreservation. A number of different commercial vitrification solutions and protocols exist; however, the core steps are largely the same. All the protocols involve multiple washing steps with ES and VS, placing the vitrified oocytes/embryos on vitrification straws, and freezing the vitrification straws in liquid nitrogen.

Manual operation for oocyte/embryo vitrification is a demanding and tedious task, for the following reasons: (1) washing oocytes/embryos with the highly viscous VS causes osmotic shock to the cells, and osmotic shock can be a major cause for cell damage; (2) most antifreezing solutes (e.g., DMSO) are toxic to ooctytes/embryos. Therefore, the washing time in toxic VS is critical but can be difficult to strictly control; (3) because of their small size (about 150 μm), oocytes/embryos can be difficult to detect and manipulate, especially when the medium surrounding the cells is dynamically changing during micropipette aspiration and dispensing; (4) the manual process has stringent skill requirements, and success rate and cell survival rate vary across different operators.

Heo et al. developed a microfluidic platform to control the loading of cryoprotectants for oocyte cryopreservation (see Y. Heo, H. Lee, B. Hassell, et al., "Controlled loading of cryoprotectants (CPAs) to oocyte with linear and complex CPA profiles on a microfluidic platform," Lab on a Chip, vol. 11, no. 20, pp. 3530-7, 2011). When an oocyte/embryo is 'parked' at a position of the microfluidic platform, one side of the oocyte/embryo directly faces the vitrification solutions while the other side does not. Accordingly, the oocyte/embryo is not exposed to VS as uniformly as in the standard manual protocols. In practice, parking embryos in a container or preset location can bring about significant difficulties for retrieving embryos after washing in VS. The timing of imposing oocytes/embryos to VS is critical because the cryoprotectants in VS can impose toxic effects on embryos if they cannot be retrieved in time.

Genea Biomedx Inc. developed an automated instrument for oocyte/embryo vitrification (U.S. Pat. Appl. Publ. No. 2013/0137080). The Genea system requires a user to manually transfer oocytes/embryos into an array of wells termed 'pods' with one oocyte/embryo in each well. In present vitrification protocols used in IVF clinics, an oocyte/embryo is moved in and out of different vitrification solutions. Differently, oocytes/embryos in the Genea system stay in the wells while vitrification solutions are dispensed into and aspirated out of the wells. Since the oocyte/embryo always sits on the bottom of the well, the cell surface in contact with the well bottom cannot be exposed to vitrification solutions as uniformly as the rest of the cell surface. Furthermore, the Genea system dispenses and aspirates fluids based on volume control without monitoring cell position; therefore, the technology cannot meet the minimal volume requirement to achieve a high cooling rate.

Similar to Genea Biomedx's automated vitrification system, patent application publication numbers WO2013020032 by Samuel S. Kim et al, US2011/0207112 by Fred Burbank et al, and WO2013098825 by Amir Arav also disclosed methods of parking oocytes/embryos in preset locations and changing VS. WO2013020032 by Samuel S. Kim et al. describes an automated device comprising a cryoprotectant holder, a cryoprotectant dispenser, and a sample holder oriented to allow a sample to be in contact with cryoprotectant from said cryoprotectant dispenser. In this device, oocytes or embryos are kept in a sample holder (e.g., electron microscopy grid) throughout the entire procedure, while the VS are dispensed in and drained out for washing the sample.

In U.S. Pat. Appl. Publ. No. 2011/0207112 by Fred Burbank et al., one or more oocytes or embryos are positioned in a processing container, the processing container being configured to allow fluid to flow into and out of the processing container, where two or more fluids flow into and out of the container.

WO20130988205 by Amir Arav disclosed a device comprising a draining zone and a capillary draining element. The draining zone is configured to hold a reproductive biological sample. The capillary draining element, whose opening is within the draining zone, is configured to drain liquid away from the draining zone while a reproductive cellular constituent of the reproductive cellular portion remains within the draining zone.

Different from the presently used vitrification protocols by placing vitrified oocyte/embryos to a straw-like carrier, US Pat. Publ. Nos. 2013/0157362 by Fuliang Du et al., 2002/0009704 by Xiangzhong Yang et al., and 2012/0251999 by Utkan Demirci et al. disclosed methods for generating micro/nano droplets of VSs comprising the biological sample, and freezing the droplets directly in liquid nitrogen.

Milton Chin disclosed in US Pat. Appl. Publ. Nos. 2009/0186405 and 2009/0123996 device designs for improving the chilling rate in liquid nitrogen and achieving the self-sealing function for storage of vitrified specimens in liquid nitrogen.

Ru et al. in Chinese Pat. Appl. Publ. No. 202918907U disclosed a semi-automated system for embryo vitrification. The system requires several key steps of manual input to conduct embryo pick-and-place. In paragraph 0056, the system requires the operator to obtain the micropipette tip position by observing from the microscope and input the position information into computer. Similar human inputs are required (see paragraphs 0062, 0070, and in 0072). The automation part is only about using robotic manipulator to pick up an embryo, move to a preset location, and place the embryo into vitrification solutions. There is no computer vision algorithm to automatically detect embryos and micropipette tip. Moreover, the technique of single cell pick-and-place with a robotic system is open knowledge, such as disclosed by Z. Lu, C. Moraes, G. Ye, C. A. Simmons, and Y. Sun in "Single cell deposition and patterning with a robotic system," PLoS ONE, Vol., 5, e13542, 2010. Additionally, the system disclosed in CN202918907U can only work with a specific Cryotip® method (see paragraph 0086), which is limited for general applications. Without washing embryos in vitrification solutions, the system cannot be used for other protocols (e.g., Kitazato's Cryotop method, and Irvine vitrification protocol) that require embryos to be washed for at least one time.

What is needed is an automated vitrification system designed to automatically process oocytes/embryos and other cell types with vitrification processing solutions, automatically place vitrified oocytes/embryos to vitrification devices (e.g., Cryotop, Cryotip®, Cryoloop, etc.), remove excessive medium from the vitrified oocytes/embryos on the devices, automatically seal the vitrification devices with caps on a sealing machine, and freeze in an automated liquid nitrogen storage tank/system.

SUMMARY OF THE INVENTION

According to one embedment of the invention, there is provided a system for automatically cryopreserve and thaw biological materials, such as cells, oocytes and embryos. The alternated system, in one embodiment, includes (a) a carrier plate having (i) an area for holding or loading the biological material, (ii) a multi-well area for holding processing solutions, and (iii) a straw area for holding one or more verification straws; (b) a first robot or robotic manipulator collected to a manipulator to manipulate the biological material and the processing solutions; (c) a second robot or robotic manipulator to manipulate the vitrification straws; (d) a microscope and an image capturing device operatively linked to the microscope to capture images of the biological material, the manipulator and the straws; (e) a computer readable medium having executable instructions; and (f) a processor for executing the executable instructions of the computer readable medium; said executable instructions including instructions for automatically: (i) processing the captured images, and (ii) operatively controlling the microscope, the image capturing device, the first robot, and the second robot.

According to one aspect of this embodiment of the present invention, the system further includes a straw-sealing machine and an automated cryopreservation storage device. and the executable instruction include instructions for automatically controlling the straw-sealing machine and the automated cryopreservation storage device.

According to another aspect of the system of the present invention, the executable instructions further include instructions for: (i) when the biological material is a cell, embryo or oocyte, detecting the cell, embryo or oocyte at different development stages from the captured images; (ii) tracking the biological material in three dimensional space; (iii) monitoring the biological material's volume; (iv) generating a concentration gradient in the treatment solutions; (v) placing the biological material on the straws; and (vi) removing excessive treatment solution from biological material placed on the straw.

According to another aspect of this embodiment the microscope is in communication with a controller including a drive for changing magnifications and focus.

According to another aspect of this embodiment the microscope include an X-Y stage for receiving the carrier plate, the X-Y stage inducing an X-axis linear motion system and a Y-axis linear motion system. In one aspect of the inventor, the executable instructions include instructions to operatively controlling the X-Y stage.

According to another aspect of this embodiment, the microscope is in communication with a controller including a driver for each of the X and Y-axis linger motion systems.

According to another aspect of this embodiment, the X-axis linear motion system and the Y-axis liner motion system are independently controllable.

According to another aspect of this embodiment the carrier plate is integrated with a heating plate to maintain a suitable temperature (for example about 37 degrees Celsius) under the biological material holding area of the carrier plate.

According to another aspect of this embodiment, the manipulator is a micropipette with a tip diameter suitable for manipulating the biological material, for example of about 100 to 200 micrometer.

According to another aspect of this embodiment the micropipette is linked to a micropipette holder, and connected to a motorized syringe.

According to another aspect of this embodiment, the micropipette is placed in the X-Z plane (i.e., perpendicular to the Y axis) at a tiling angle with the tip side down.

According to another aspect of this embodiment, the system further includes a motorized syringe in communication with a controller including a driver to control the linear motion, and the executable instruction include instructions for automatically controlling the motorized syringe.

According to another aspect of this embodiment, the micropipette holder is coupled to the first robotic manipulator.

According to another aspect of this embodiment, the first robotic manipulator has at least three degree of freedom along X, Y and Z.

According to another aspect of this embodiment, the first robotic manipulator is in communication with a controller including a driver for each of the X, Y, and Z axis linear motion system.

According to another aspect of this embodiment real-time images are captured from the microscope and image capturing device at a frame rate of 30 frames per second or higher to provide the system with continuous visual information.

According to another aspect of this embodiment, when the biological material is an embryo, the system is capable of automatically defecting embryos at different development stages (e.g., 2-cell, 4-cell, and blastocyst) from the captured images.

According to another aspect of this embodiment, the system further includes a biological material detection algorithm.

According to another aspect of this embodiment, the system is capable of automatically focusing on the objects by maximizing focus measures.

According to another aspect of this embodiment, the biological material detection algorithm further includes an adaptive threshold algorithm to binarize the gray scale image.

According to another aspect of this embodiment, the biological material detection algorithm further detects the contours of all objects in the binarized image.

According to another aspect of this embodiment, the objects having contour area in a specific range are considered as potential biological material targets.

According to another aspect of this embodiment, in order to avoid false detection, the contours of potential biological material targets are further fitted to circles by using a Hough transform algorithm, and the center point of the circle is considered to be the biological material position.

According to another aspect of this embodiments the system is capable of automatically detecting the micropipette tip from the captured images.

According to another aspect of this embodiment, the micropipette tip detection algorithm further includes two Sobel filters along both x and y axis.

According to another aspect of this embodiment, the Sobel filter along y-axis is used to determine the outside walls of the micropipette, and the Sobel along x-axis is used to determine the tip position.

According to another aspect of this embodiment, the outside walls of the micropipette are further detected by using a Hough line transform algorithm.

According to another aspect of this embodiment, the outside walls of the micropipette tip are used to determine a region of interest (ROI) for biological material determine when the biological material is aspirated into the micropipette.

According to another aspect of this embodiment, the relative distance between micropipette tip and biological materials along a Z axis is determined by a contact detection algorithm that is based on detecting a horizontal sliding motion when the tip of the micropipette contacts a substrate that holds the biological materials (for example a culture dish).

According to another aspect of this embodiment the robotic manipulator moves the micropipette tip close to a target biological material via closed-loop visual servo control.

According to another aspect of this embodiment, the motorized syringe is used to generate a negative pressure to aspirate target biological materials into the micropipette tip after the tip is moved close to the biological material.

According to another aspect of this embodiment, the motorized syringe is also used to generate a positive pressure to dispense the target biological material from the micropipette tip into a desired location.

According to another aspect of this embodiment, a computer vision algorithm is used to detect the biological material's position inside the micropipette.

According to another aspect of this embodiment, the biological material is precisely postponed to a desired location insider the micropipette via closed-loop visual servo control by controlling the motorized syringe.

According to another aspect of this embodiment, the biological material is automatically moved from one location to another location (e.g., transfer from culture dish to multi-well plate).

According to another aspect of this embodiment, the biological material is automatically washed in vitrification solutions by repeating the biological material aspiration and dispensing.

Acceding to another aspect of this embodiment, the system is capable of automatically tracking biological materials in 3D space when the biological material is transferred from ES to VS.

According to another aspect of this embodiment, the system is able to automatically generate a concentration gradient in VS by coordinately moving micropipette tip and dispensing ES of low concentration.

According to another aspect of this embodiment, the system is capable of automatically monitoring the biological material's volume change in real time to provide a criterion for optimizing the washing time in different types of solutions.

According to another aspect of this embodiment, the vitrified biological material is automatically taken out from VS via micropipette aspiration when it teaches the minimum volume.

According to another aspect of this embodiment, the biological material is automatically placed onto a vitrification straw after washed in VS.

According to another aspect of this embodiment the verification straw position is automatically detected by a computer vision algorithm.

According to another aspect of this embodiment, vitrification straw detection further includes a Hough line transform algorithm to detect the two horizontal edges of the straw.

According to another aspect of this embodiment, the vertical distance between micropipette tip and vitrification straw is detected by contact detection that is based on the vitrification straw tip's deflection motion caused by the micropipette tip's contact.

According to another aspect of this embodiment, the micropipette tip is automatically moved to the center of the vitrification straw and contacts the straw surface.

According to another aspect of this embodiment, the vitrified biological material is dispensed on the straw by controlling the motorized syringe to apply a positive pressure.

According to another aspect of this embodiment, excessive medium around the biological material is automatically aspirated away by the micropipette at a location with a distance (e.g., 300 micrometer) away from the position where the biological material is dispensed.

According to another aspect of this embodiment, the aspiration of excessive medium is automatically stopped when the volume of the biological material droplet on the straw does not change further.

According to another aspect of this embodiment, the vitrification straw with vitrified biological materials on the tip is picked up from the carrier plate by a robot.

According to another aspect of this embodiment, the robot plunges the vitrification straw with vitrified biological materials on tip into liquid nitrogen in a sub-container for fast freezing.

According to another aspect of this embodiment, the vitrification straw after freezing is placed on the sliding part of a sealing machine.

According to another aspect of this embodiment, the sealing machine, preloaded with vitrification straw caps, caps the straws by moving the siding part.

According to another aspect of this embodiment, the vitrification straw sealed with the cap is inserted in a slot of the sub-container containing liquid nitrogen.

According to another aspect of this embodiment, the sub-container is automatically transferred into an automated liquid nitrogen storage system for long-term cryopreservation.

According to another aspect of this embodiment, the washing solution types and soaking time can be readily specified via the software interface of the system, according to different vitrification kits and protocols.

According to another aspect of this embodiment, the system is capable of processing multiple biological materials with an optimized schedule for saving the total processing time.

Embodiments of the present invention provide also for automated methods for cryopreserving and thawing biological material, particularly oocytes, embryos, and other cellular materials using the systems of the present invention. In one embodiment of the present invention, a method for processing biological materials include, (a) automatically (i.e., not human operator assisted) and uniformly exposing the biological material to a series of vitrification processing solutions, thereby obtaining vitrified biological material, (b) automatically placing the vitrified biological material on the surface of a vitrification straw, (c) automatically dipping or plunging the vitrification straw carrying the vitrified biological material in cryopreservation solution, (d) automatically sealing the vitrification straw carrying the vitrified biological material, (a) automatically storing the sealed vitrification straw in cryopreservation solution thereby freezing the vitrification straw with the vitrified biological material for long term cryopreservation.

In another embodiment of the method of the present invention, the method further comprises automatically retrieving the frozen seated vitrification straw from the cryopreservation solution, and automatically and uniformly exposing the frozen vitrified biological material to a series of processing solutions, thereby thawing the biological material.

BRIEF DESCRIPTION OF THE DRAWINGS

The following figures illustrate various aspects and preferred and alternative embodiments of the invention.

DESCRIPTION OF THE INVENTION

Definitions

Figure 1:
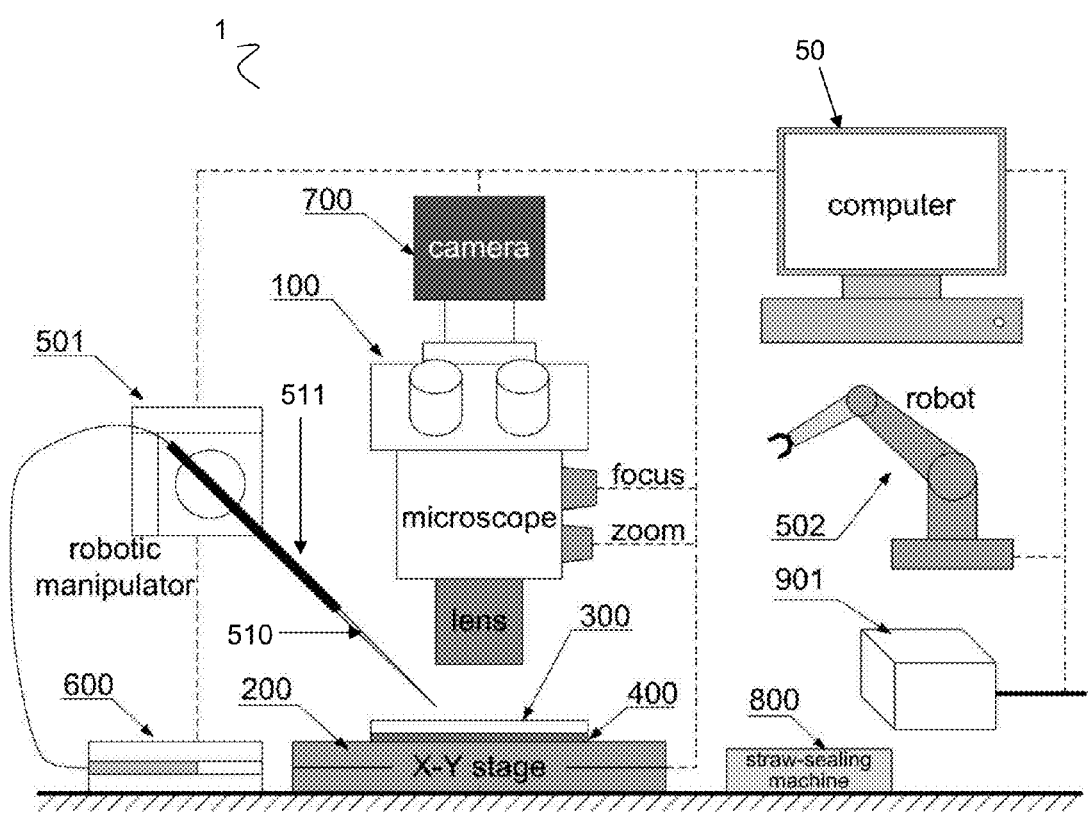
FIG. 1 illustrates an automated robotic vitrification system in accordance to one embodiment of the present invention.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. All documents cited are incorporated herein by reference in their entirety. In order to aid in the understanding and preparation of the within invention, the following illustrative, non-limiting, examples are provided.

"Automatic/automated" as used in this document means free of human operator control (for example manual and/or joy-stick based control) or where human intervention is limited to entering input data. Software (image processing and motion control) and hardware are integrated in a computer machine to reduce or eliminate the operator's intervention.

"Motorized" as used in this document means that devices such as positioning devices, syringes and so forth, are equipped with a motor or motors which are controlled via control algorithms and strategies.

Overview

The present invention relates to hardware components and computer vision algorithms to automate visitation process, including full automation. The present invention may be used to implement vitrification kits/protocols. For instance, the Kitazato's kit/protocol (Kitazato Inc., Cryotop Safety Kit Protocol, 2014) and the Origio Vitrification protocols (Origio MediCult Media, Medicult Vitrification Cooling Protocol, 2014) can be followed in the robotic system of the present invention by simply changing the oocyte/embryo washing time in vitrification solutions.

The robotic system of the present invention is designed to be fully automated, including automated biological material loading and retrieval. The system monitors the response of individual cells in vitrification solution (VS) to determine the optimal washing time in VS. After washing cells in VS, the verified embryos are automatically placed onto vitrification straws. The straws are then sealed with a cap on a cap-sealing machine. The sealed straws are picked up and frozen in a cryopreservation sub-container, such as a liquid nitrogen sub-container. The sub-container containing the frozen vitrification straws is finally placed in an automated liquid nitrogen system for long-term cryopreservation. The robotic system performs tasks in an optimized parallel way to process multiple cells or cell lines. The system also allows users to readily specify the operation time of each step for realizing different verification protocols or for developing new protocols.

A. Automated Vitrification System

Embodiments of the invention relate to a system that includes a motorized X-Y stage microscope movable in two axes for moving sample in the X-Y plane, a camera for capturing images, a robot for positioning a manipulator, such as a micropipette, a motorized syringe connected with the micropipette for aspirating and dispensing embryos/oocytes/cells (biological materials), a carrier plate for holding the biological material culture dish, a multi-well plate for holding processing solutions, such as vitrification and thawing solutions, and multiple vitrification straws, a second robot for handling vitrification straws, and an automated liquid nitrogen storage system for long-term cryopreservation of the vitrified samples. This section describes an embodiment of the hardware system, the system work flow, and technical details.

Vitrification straws may be described as physical carriers to hold embryos for freezing and cryopreserving in, for example, liquid nitrogen. Vitrification straws can be classified into three groups: opening strip based straws (e.g., Cryotop), micropipette based straws (e.g., Cryopipette), and CPA (cryoprotective agent) film based straws (e.g., Cryoloop). The opening strip based straws often consist of a polypropylene strip attached to a hard plastic handle. Vitrified embryos are placed directly on top of the strip. After placing embryos on strip, the straws are sealed with plastic caps to avoid contaminations in long-term cryopreservation. The micropipette based straws use micropipettes to directly aspirate vitrified embryos. After the vitrified embryos are aspirated into the micropipette, the opening of the micropipette is sealed by a heat sealer. The CPA film based straw, taking Cryoloop for example, involves a plastic loop that can be integrated into a lid of a cryovial via a stainless steel stick. During vitrification, the $Cryoloop^T$ is immersed into a cryoprotective solution to create a thin film of the solution inside the loop. The vitrified embryos are then transferred into the film and sealed in the cryovial. In this document, the term "vitrification straw" refers to all three classification groups. Among all the vitrification straws, Cryotop is a well-accepted method because it involves least residual solutions surrounding vitrified embryos for producing the highest cooling rate and highest post-thawing cell survival rate. Accordingly, herein Cryotop is used as an example to explain the present invention.

In one embodiment with reference to FIG. 1, the vitrification system 1 of the present invention may include a microscope 100 which may be equipped with motorized magnification and motorized focusing functions. Mounted on or linked to the microscope may be an XY motorized stage 200. A custom designed carrier plate 300 with a heating plate 400 may be placed on the XY stage 200. As further described herein below and illustrated in FIG. 2, the carrier plate 300 may be configured to hold a biological material culture dish 301, a multi-well plate 302 containing biological material processing solutions, and multiple vitrification straws 303. A first robot 501 or robotic manipulator carrying a micropipette 510 may be used to manipulate biological materials such as oocytes/embryos/cells which may be held in culture dish 301. A motorized syringe 600 may be controlled to aspirate or dispense biological materials into and out of the micropipette 510. A camera 700 may be coupled or connected to the microscope 100 to provide visual feedback that may be used to realize vision-based robotic control. The camera 700 may be at a frame rata of 30 frames per second or higher to provide the system with continuous visual information. A second robot 502 may be used to handle vitrification straws for freezing in liquid nitrogen. As part of the system 1, a straw-sealing machine 800, which may also be custom aligned, may be used to seal vitrification straws with caps. Additionally, a liquid nitrogen (or other cryopreservation solution) sub-container 901 may be designed to carry frozen straws and is stored in an automated liquid nitrogen storage system 902. The system 1 may also include a central computer 50 having instructions that when executed control all the aforementioned hardware and functions via running custom developed control software.

The system 1 shown in FIG. 1 may include an upright microscope 100. The microscope 100, may include a motorized X-Y stage 200. The stage 200 may have a travel range of centimetres and a resolution better than 1 µm along each axis. The microscope 100 may have a range of magnifications (e.g., 0.7x-11.5x), which may be automatically changed by the system's control program. In addition, the focus of the microscope may also be changed by the system automatically via auto-focusing algorithms.

Figure 2:
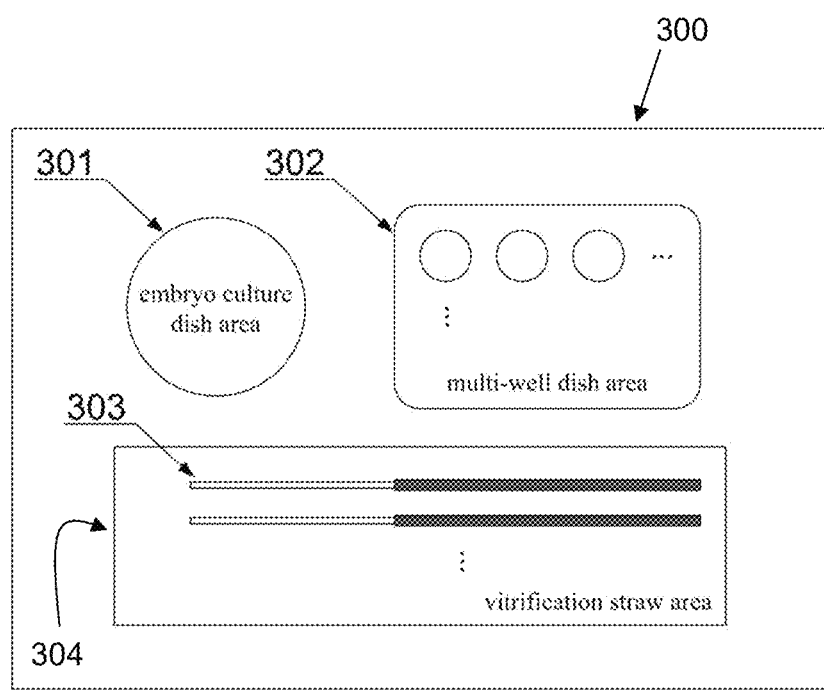
FIG. 2 illustrates a top view of a carrier plate that holds an embryo culture dish, a multi-well plate, and multiple vitrification straws in accordance to one embodiment of the present invention.

As shown in FIG. 2, the carrier plate 300 may include any number of working areas, for example three working areas; a biological material loading area 301, a biological material processing (i.e. washing, equilibration, vitrification, thawing and so forth) area 302, and a vitrification straw area 304. The biological material loading area 301 may be for holding a standard biological material culture dish (e.g., 35 mm Petri dish). The biological material processing area 302 is for holding a multi-well plate that may include processing solutions such as equilibrium solution (ES), vitrification solution (VS), washing solution, flawing solution, which may be used for washing/soaking biological material. The vitrification straw area 304 may include multiple slots for holding vitrification straws 303. A carrier plate having more or less than three working areas may also be possible.

The biological material, such as embryos, oocytes or cells, in dish 301 may be manipulated by using a manipulator, such as micropipette 510. The micropipette may have a tip diameter suitable for aspirating or dispensing the biological material. In the case of embryos, the micropipette may have a tip diameter in the range of about 100-200 micrometer. The micropipette may be inserted into a micropipette holder 511 connected to the motorized syringe 600. The micropipette holder 511 is clamped to a robotic manipulator 501, which has a travel range of centimetres and a resolution better than 1 µm along each axis.

After processing biological material on the carrier plate 300 (i.e., washing biological material with a series of VS, then placing biological material on the vitrification straw), a vitrification straw 303 with vitrified biological material on top may be picked up by a second robot 502 that plunges or dips the straw into liquid nitrogen in a sub-container 901 for fast freezing. The frozen vitrification straw may then be placed by the robot to a cap-sealing machine 800 for sealing vitrification straw with a plastic cap. The sealed straw may finally be inserted into the storage slots of the sub-container, and the sub-container is transferred by the robot 502 into an automated liquid nitrogen storage system 902.

Robots 501 and 502 may be multiple degrees of freedom robots. In one embodiment, robots 501 and 502 may have at least three degrees of freedom. One robot may serve to position the micropipette to pick and place cells and solutions, and the other robot may be used to handle vitrification straws.

Figure 11:
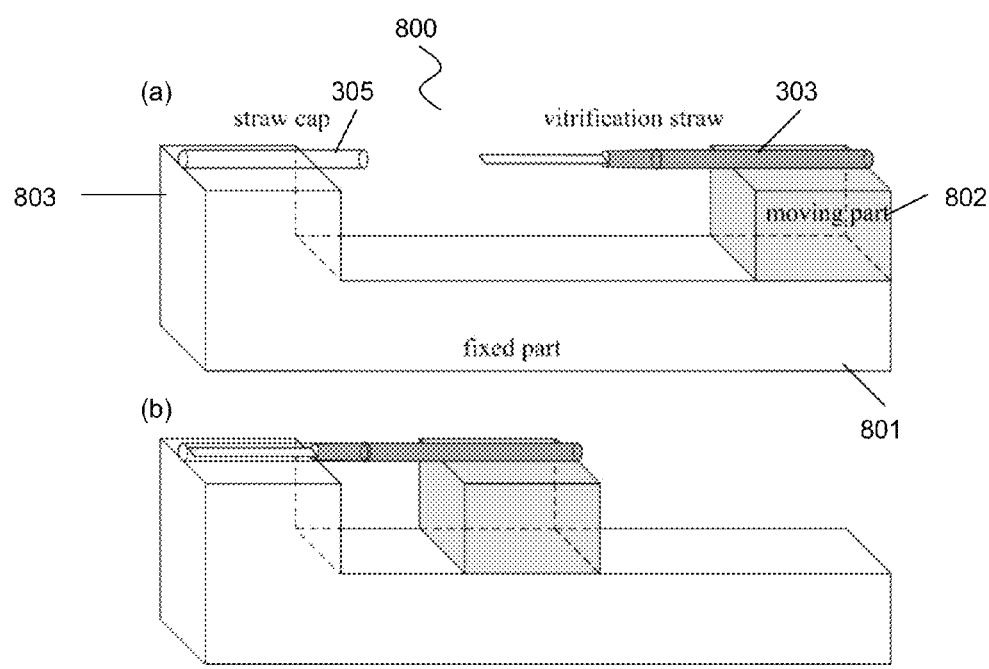
FIG. 11 Schematic showing an example of a straw cap seeing machine that places a cap on the vitrification straw in accordance to one embodiment of the present invention.

With reference to FIG. 11, the straw-sealing machine 800 may include a fixed part 801 and a moving part 802. The fixed part 801 may include a shoulder 803 extending from one end of the fixed part 801. The moving part 802 may be configured to slide on an upper surface of the fixed part 801 towards the shoulder 803. In one embodiment of the present invention, the shoulder 803 may be configured for receiving and holding a straw cap 305. The moving part 802 may be configured to receive and hold a vitrification-type straw 303. In this case, sliding movement of the moving part 802 will result in the vitrification straw 303 sliding into cap 305 and sealing of the vitrification straw (see FIGS. 11(a) and 11(b). In another embodiment, the shoulder 803 may receive and hold the straw while the moving pert 802 may receive and hold the cap such that the cap moves towards straw thereby sealing it.

B. Automated Embryo Vitrification Work Flow

Figure 3:
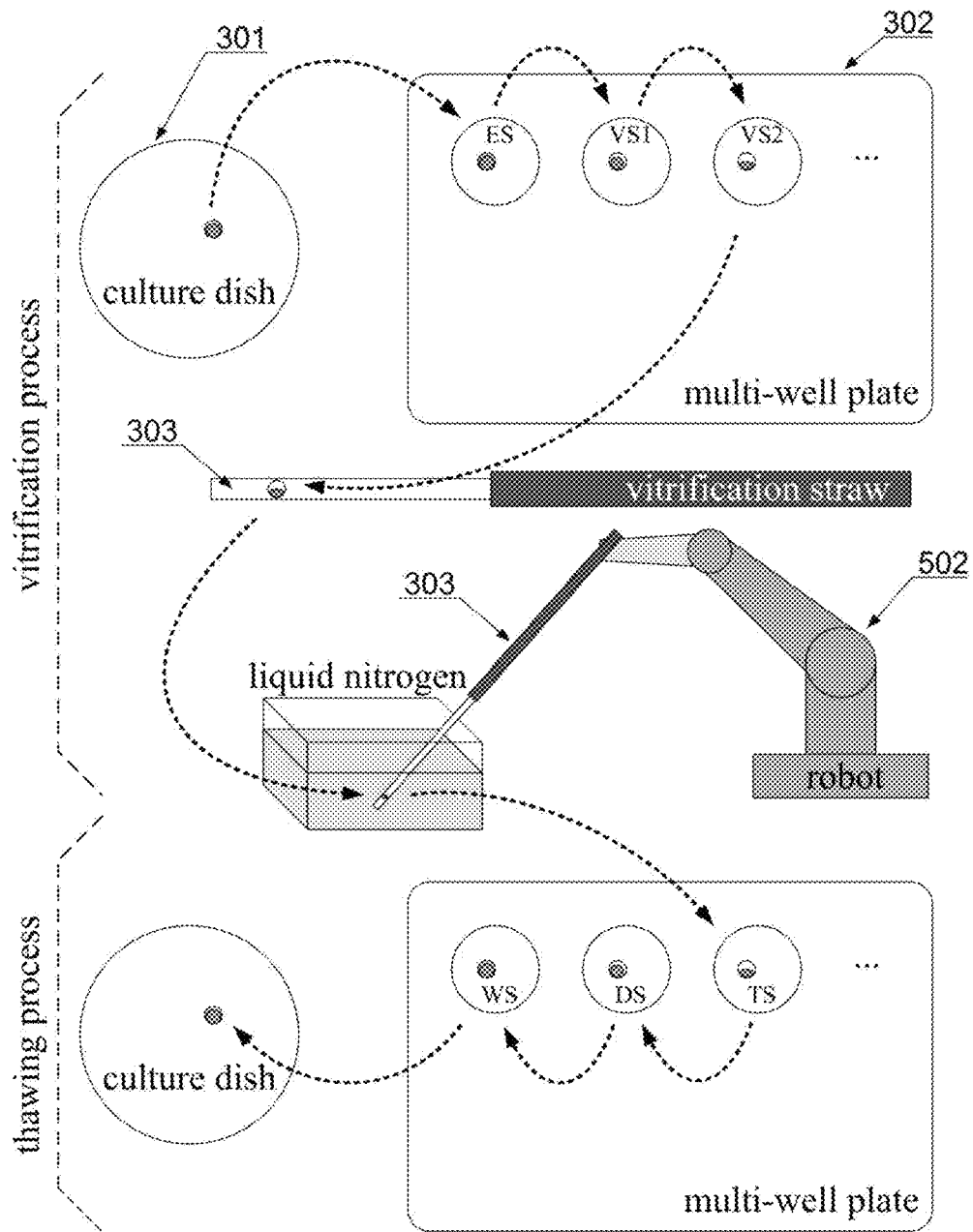
FIG. 3 is a graph illustrating an example protocol for vitrification and thawing process. ES: equilibrium solution, VS: vitrification solution, TS; thawing solution, DS: diluent solution, WS: Washing solution.

The vitrification work flow described below is explained by using the implementation of Kitazato vitrification protocol as an example. The system of the present invention may also be capable of automating the implementation of other protocols, such as that of Origio Vitrification protocols. FIG. 3 schematically shows major steps of a method of automated biological material vitrification in accordance to one embodiment of the present invention. The examples is with regards to embryos, however it should be understood that the system is also capable of automatically processing other types of biological materials, such as oocytes and any other biological cells. In the following example, the micropipette's tip is shown to point in the right direction. Accordingly the terms "left" and "right" are used relative to the micropipette's tip direction. It should be understood that the system may be reversed and have the micropipette's tip pointing to the left direction. The example processes described below and illustrated in FIG. 3, with reference to FIG. 1, may be implemented as machine-accessible instructions utilizing any of different programming codes stored in computer 50.

Step 0. System Setup and Preparation

The set up step is the only step which may include sub-steps that may involve an operator. All other steps in the method are fully automated.

(a) Upon being turned on, the system 1 automatically moves the X-Y stage to a home position (i.e., the bottom right corner) and turns on the heating plate.
(b) Embryo culture dish is taken out from incubator and placed to the embryo loading area on the carder plate 300. The culture medium may be covered with mineral oil to prevent evaporation for maintaining a constant pH.
(c) ES (equilibrium solution) and VS (vitrification solution) are added to the multi-well plate 302 according to the protocol provided by the vitrification kit supplier.
(d) Vitrification straws 303 are placed in the straw slots 304 of the carrier plate 300.

Step 1. Automated Pick-Up of Embryos from Culture Dish (a) The system portions the embryo loading area into the field of view (FOV) under the microscope 100.
(b) Autofocusing is performed to focus on embryos.
(c) Detect embryos from the captured images.
(d) Detect micropipette 510 tip and position it to the center of FOV under the microscope.
(e) Detect the tip's contact on dish substrate by lowering the micropipette towards the dish bottom.
(f) Move a target embryo close to the micropipette tip position by moving the X-Y stage 200 via closed-loop visual servo control.
(g) Aspirate the embryo into the micropipette and position it to a desired location inside the micropipette by controlling the motorized syringe.
(h) Move micropipette up (e.g., by 3000 µm) above the dish bottom surface, and move X-Y stage to ES area of multi-well plate 302.

Step 2. Alternated Washing of Embryos in ES (a) System 1 performs autofocusing to focus on the bottom of ES region on the multi-well dish area 302.
(b) The micropipette is lowered until contact with the bottom of ES region is detected.
(c) The embryo is dispensed into ES by applying a positive pressure from the motorized syringe.
(d) Embryo is washed for several times by repealing micropipette aspiration and dispensing.
(e) The embryo is kept in ES for a suitable period of time (e.g., 12 min as in Kitazato protocol). The embryo shrinks to the minimum volume and then gradually returns to is ordinal volume, which indicates that equilibration is complete. The washing time in ES may be optimized for each of embryos according to their individual volume change in ES, enabled by constantly monitoring embryo volume by the system.

(f) Aspirate and position the embryo in micropipette by controlling the motorized syringe.

(g) Move micropipette up (e.g., by 3000 μm) above the dish bottom, and move X-Y stage to VS area of the multi-well dish 302.

Step 3. Automated Washing of Embryos in VS (a) System performs autofocusing to focus on the bottom of VS region on the multi-well dish area 302.

(b) The micropippette is lowered until contact with the bottom of VS region is detected.

(c) The embryo is dispensed into VS. Due to the higher concentration of VS, the embryo equillibrated in ES floats upwards in VS, which cause embryo's position to change along the Z axis. The system 1 detects the embryo in 3D space by real-time processing 2D images and moving the focal plane upwards to keep the embryo in focus. Sub-steps (a), (b) and (c) may be repeated if multiple washing steps in VS is required by a protocol (e.g., Kitazato protocol requires VS1 and VS2).

(d) Aspirate and position the embryo in micropipette when the embryo is detected to have its minimum volume or at fixed time indicated by the vacation protocol.

(e) Move micropipette up (e.g., by 3000 μm) above the dish bottom, and move X-Y stage to the vitrification straw area 304.

Step 4. Automated Placing of Embryo on Vitrification Straw (a) System 1 performs visual servo control of the X-Y stage 200 to position a vitrification straw 303 to the center of FOV.

(b) The micropippette is lowered until its tip contacts the vitrification straw's surface.

(c) Control the motorized syringe to infuse a relatively large volume (e.g., 5 μL) of vitrification solution (VS) in order to ensure that embryo is dispensed out of the micropipette and onto the surface of the vitrification straw.

(d) Move the micropipette tip away from is initial position on the straw surface to the left side of the FOV. Medium follows the micropipette tip because of surface tension.

(f) Aspirate away excessive medium until the volume of embryo droplet does not change further on the straw.

(g) Move micropipette up (e.g., by 3000 μm) above the vitrification straw, and move the X-Y stage to the home position.

Step 5. Automated Freeze, Seal and Cryopreserve the Vitrification Straw (a) The vitrification straw 303 with vitrified embryo on top of its surface is picked up by the second robot 602 and immediately frozen in the sub-container 901 containing liquid nitrogen.

(b) Place the frozen straw on the cap sealing machine 800.

(c) Move a plastic cap to seal the straw tip via a guiding mechanism on the sealing machine.

(d) Insert the sealed frozen straw into a slot in the liquid nitrogen sub-container 901.

Figures 4, 5:
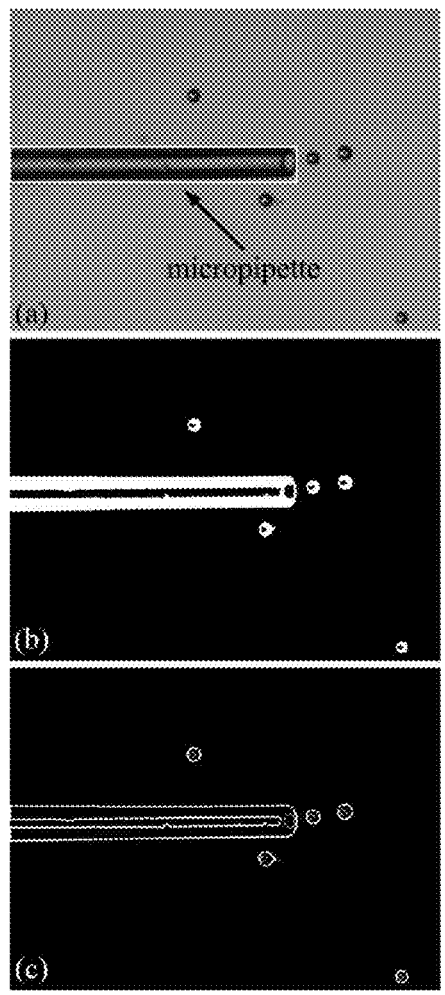
FIG. 4 is a graph illustrating an example schedule for parallel vitrification by the robotic system of the present invention. In this example, processing time follows the protocol from Kitazato Company (Kitazato Inc., Cryotop Safety Kit Protocol, 2014).
FIG. 5 are images showing an example algorithm for micropipette detection of using area and shape information of abbots contained in the images. (a) The rectangle is the detection result. (b) Binarized image shows the defected foreground objects. (c) Contour image shows the micropipette shape; a Hough line transform is applied to reject false detections of micropipette.

(e) Transfer the sub-container into the automated liquid nitrogen storage system for long-term cryopreservation Typically, more than one oocyte/embryo/cell needs to be processed within a batch. In order to shorten system idle time, task scheduling may be made/optimized. FIG. 4 shows a scheduling example, assuming Kitazato vitrification protocol is implemented. Accordingly to this scheduling, robot 501 starts to pick up the second embryo from the culture dish while the first embryo is inside ES.

C. Thawing Process

The set up step is the only step which may include sub-steps that may involve an operator. All other steps are fully automated.

Step 0. System Setup and Preparation (a) System 1 is turned on for thawing process and moves the X-Y stage to home position.

(b) Pre-warmed thawing solution (TS), dilution solution (DS), and washing solution (WS) are added into the multi-well dish, according to the protocol.

(c) The frozen straw with embryos is taken out from the alternated liquid nitrogen storage system. The sealing cap is removed from the straw by the second robot 502.

(d) The straw is plunged into TS. The straw is gently shaken to let embryos fall off from the straw tip.

Step 1. Automated Thaw Embryos in TS (a) The system moves the TS region to the center of FOV under the microscope.

(b). Autofocusing is performed to focus on the embryos.

(c). Embryos are detected and tracked from captured images.

(d). Embryos are kept in TS for a suitable period of time (e.g., about 1 min), according the protocol being used.

(e). Micropipette tip is detected and positioned to the center of FOV under the microscope.

(f). The tip's contact on dish substrate is detected by lowering the micropipette towards the dish bottom.

(g). A thawed embryo is moved close to the micropipette tip position.

(h). The embryo is aspirated into the micropipette and positioned to a desired location inside the micropipette by controlling the motorized syringe.

(i). Micropipette is moved up (e.g., by about 3000 μm) above the dish bottom, and move X-Y stage to DS area.

Step 2. Automated Transfer Embryos from TS to DS (a). Autofocusing algorithm is performed to focus on the bottom of DS region on the multi-well dish.

(b). The micropipette is lowered until contact is detected.

(c). The embryo is gently dispensed to the bottom of DS by applying a positive pressure from the motorized syringe.

(d). The embryo is kept in ES for a period of time (e.g., 3 min), according to the protocol.

(e). The embryo is aspirated and positioned in the micropipette by controlling the motorized syringe.

(f). Micropipette is moved up (e.g., by about 3000 μm) above the dish bottom, end move X-Y stage to WS area.

Step 3. Automated Wash Embryos and Transfer to Culture Medium (a). The steps as in Step 2 may be repeated to transfer embryo from DS to WS, and keep embryo in WS for a suitable period of time (e.g., 5 min) according to the protocol being followed.

(b). Embryos are washed in WS for a number of times, for example two, three, four or more times, by aspirating the embryos into micropipette and gently placing it on the top of WS. The embryo may be let to freely fall to the bottom of WS. System detects embryos and tracks them in 3D space during washing in WS.

(c). Washed embryos are transferred to a culture dish containing the culture medium, similar to Step 2.

(d) Put the embryo culture dish back to a 37° C. incubator for complete recovery.

D. Techniques for Automated Vitrification

Techniques for implementing the work flow discussed in the previous section are described below. These techniques include: micropipette/vitrification straw detection, contact detection, autofocusing, embryo detection/tracking, positioning embryos in micropipette, generation of a moderate concentration gradient in VS, removal of excessive VS from the vitrification straw, a vitrification straw sealing machine, and an automated liquid nitrogen storage system. The techniques described below and illustrated in the referred figures may be implemented as machine-accessible instructions utilizing any of different programming codes stored in computer 50.

Detection of Micropipette and Vitrification Straw

The first step may be to binarize an image of the micropipette or vetrification straw and extract target objects from the background. In IVF clinics, stereo up-right microscope is often used for examining the inner morphological detail of embryos. Stereo microscope produces a lighting gradient on the captured images. The system runs a histogram-based thresholding algorithm to discriminate foreground objects (e.g., micropipette, or vitrification straw) from background. At first, a histogram of gray scale value of all pixels may be calculated. The histogram may include two peaks, with one representing the background pixels and the other representing the pixels of the foreground objects. The middle point of the two pixels may be used by the system as threshold to bitwise the image for extracting foreground objects, as shown in FIG. 5(a)(b).

After image binarization, morphological transformations (i.e., erosion and dilation) are performed to remove the noisy objects of small sizes. Since the micropipette is much larger than embryos, the largest object in the binarized image is taken by the system to be the micropipette. In addition to using size as a criterion for detecting micropipette, the shape information is also used by the system to ensure correct defection. The outside walls of the micropipette can be modeled as two lines, therefore, Hough line transform is applied on the contours of detected objects (see FIG. 5(e)). If the two lines are on the largest object, micropipette detection is confirmed to be correct. Otherwise, it is considered as a false detection.

In the robotic system, the micropipette tip points to the right direction. According to this specific system setup, the point (on the detected micropipette object) with the largest distance to the left boundary of the image is considered by the system to be the micropipette tip position. Within the detected micropipette, a smaller region is extracted as a region of interest (ROI) for detecting embryos inside micropipette.

The detection of vitrification straw is similar to micropipette detection. The difference is that the orientation of the vitrification straw (with the tip pointing to the left side) is opposite to the micropipette.

Contact Detection

The relative distance along Z axis between micropipette tip and dish bottom or vitrification straw's surface may be critical for successful automation of picking/placing embryos from/to dish or straw.

Figure 6:
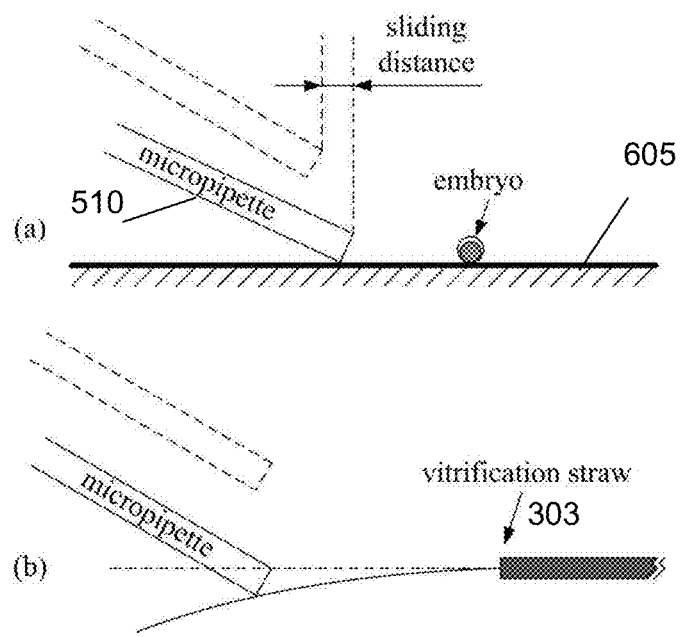
FIG. 6 is a graph illustrating contact detection algorithms for determining micropipette's Z position in accordance to one embodiment of the present invention. (a) Front view illustrating that the micropipette tip produces horizontal sliding movement when contacting the embryo culture dish substrate. The Z position of the micropipette relative to the culture dish bottom is determined by detecting this horizontal sliding motion. (b) Front view showing that the micropipette tip deforms the vitrification straw tip when contacting the straw tip surface. The Z position of the micropipette tip relative to the vitrification straw tip is determined by detecting the straw tip's deformation.

The relative distance between micropipette tip and dish bottom may be detected based on detecting micropipette tip's sliding motion on the dish bottom. The system constantly visually tracks the tip's position in the x-y plane, while lowering the micropipette downwards to the dish bottom. As illustrated in FIG. 6(a), when the micropipette 510 tip contacts the dish bottom 601, further downward movement induces the tip's horizontal sliding motion on the dish bottom, which changes the tip's position in the x-y plane. The detected Z position of the robotic manipulator 501 is then recorded as the reference height of the dish bottom.

The detection of the micropipette tip's contact on vitrification straw is based on a different principle. The vitrification straw 303 has low stiffness and is easily deflected when contacted by the micropipette tip. Therefore, the robotic system of the present invention detects the contact between micropipette tip and straw by detecting the straw's deformation motion (see FIG. 6(b)). Various motion detection algorithms can be used to detect straw's deformation, such as frame subtraction, background subtraction, optical flow, or the motion history image method.

Another method for detecting the tip's contact with vitrification straw is based on detecting the spreading of medium on the straw. When micropipette tip contacts the straw, medium inside the micropipette passively flows out to the hydrophilic straw surface, due to surface tension. Therefore, the contact position can be determined by detecting medium spreading around the micropipette tip. When an object appears around the tip position in the binarized image, contact is considered detected. The robotic manipulator 501 then stops downward movements and records the reference Z position.

Autofocusing

One prerequisite stop for the aforementioned detection processes is to focus on a reference surface (i.e., on dish bottom or on straw surface). Accordingly, the system conducts auto-focusing. The autofocus algorithm uses a focus measure based on Tenenbaum gradient to determine the focus level of the captured image. This algorithm convolves an image with Sobel operators, and then sums the square of the gradient vector components. The system adjusts the microscope focal plane until the focus measure reaches maximum. The first order derivative of focus measure is used to determine the maximal value. When the focal plane moves to the target objects (e.g., embryos or micropipette tip), the focus measure is increasing and the first order derivative is positive. Once the first order derivative turns to negative, the local plane has reached the optimal position at the turning point and starts to move away from the target objects.

Embryo Detection/Tracking

Figure 7:
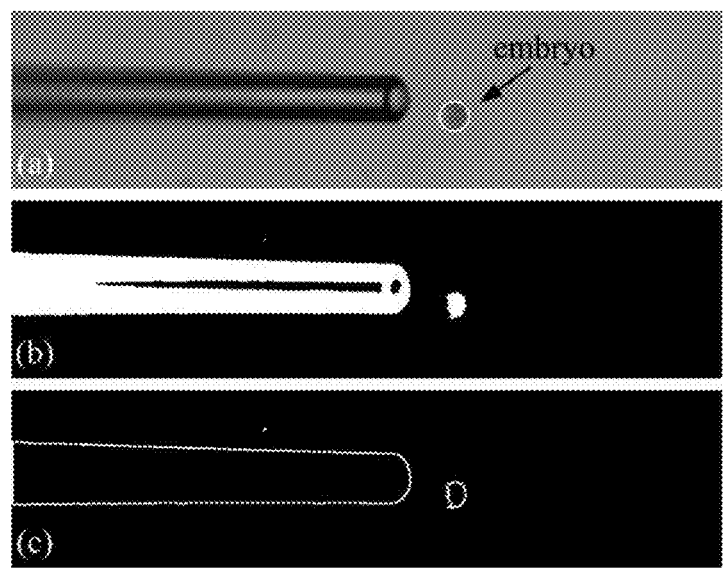
FIG. 7 is a graph illustrating an example method for embryo detection in accordance to one embodiment of the present invention. (a) The circle shows the detection result. (b) Binarized image shows the detected foreground objects. (c) Contour image shows the shape information: a Hough circle transform is applied to fit a circle to the potential embryo target, in order to avoid false detections.

In order to avoid the loss of embryos through the entire vitrification process, robustly detecting and tracking embryos is important. With reference to FIG. 7, the first step in the system to detect embryos is image binarization [see FIG. 7(a)(b)]. In the binarized image, the system detects embryos from foreground objects by using area and shape information. Objects with an area ranging from 500 to 1000 pixels are considered to be potential embryo targets. In addition, a Hough circle transform is applied to fit circles on the potential targets. The objects with circular shapes are considered as embryos. The number of fitted circular shapes indicates the embryo developmental stages (e.g., 2-cell, 4-cell, blastocysts stage). The area of an individual embryo is monitored in real time by the system to provide a criterion for optimizing the immersion time in VS. When washing embryos in VS, the embryos shrink in the beginning due to osmatic pressure. Then they re-expand to equilibrate with VS. Since the solute of VS is toxic, the equilibration with VS should ideally be avoided. Therefore, embryos ideally should be taken out of VS once they reach their minimum size/volume. However, in present manual operation, all embryos undergo the same timing.

In order to rapidly locate embryos in the relatively large culture dishes, the embryo detection algorithm further involves the change of the microscope magnifications and the movement of the X-Y stage. The system first detects potential embryo objects under a lower magnification (i.e., larger FOV). Then the potential embryo objects are positioned to the center of FOV by moving the X-Y stage. The system then automatically switches the microscope to a higher magnification, and performs embryo detection again to verify the detection result from under lower magnifications and analyze the inner morphology of the embryo.

When transferring embryo from lower-concentration ES to VS or during the washing steps, embryos can move up and down inside the solutions, due to the buoyancy force and/or fluidic flow caused by micropipette movement/dispensing. In order to tracking embryos in 3D space, the embryo detection algorithm is integrated with the autofocusing algorithm by dynamically moving the focal plane to keep the tracked embryo(s) in focus.

Positioning Embryos in Micropipette

Figure 8:
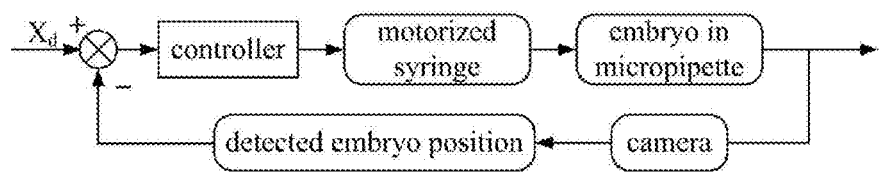
FIG. 8 Control diagram for positioning embryos inside micropipette in accordance to one embodiment of the present invention.

During embryo aspiration and dispensing, the robotic system quickly and accurately positions the embryo in micropipette. The embryo's position is visually tracked to provide position feedback for the system to realize closed-loop visual servo control. The desired position inside the micropipette is at a pre-specified distance to the tip. This distance cannot be too long because it would introduce too large a volume of the solution when dispensing the embryo into the next vitrification solution. On the other hand, the distance cannot be too short because the embryo can possibly 'escape' out of the micropipette tip, resulting in oocyte/embryo loss. Based on the error between desired position and detected positions, the system runs a controller (e.g., proportional-integral-derivative (PID) or robust controller) algorithm to control the motorized syringe and aspirate or dispense until the oocyte/embryo reaches the desired position. FIG. 8 shows a control diagram for positioning embryos in micropipette.

Generation of a Moderate Concentration Gradient

In vitrification, ES often has the same solute as VS but at a lower concentration. After equilibrated in ES, the embryo encounters an osmotic shock when transferred into VS due to the concentration change. In order to lessen cell damage, this osmotic shock may be minimized. Therefore, the robotic system may generate a moderate concentration gradient in VS. To generate a moderate concentration change, the system moves the micropipette along the X axis to the left while dispensing ES into VS. ES medium is dispensed at a constant rate (e.g., at 5 µl/sec) while the speed of micropipette movement keeps increasing until micropipette tip is moved to the edge of FOV. Since the mixing rate between ES and VS is constant, a concentration gradient is generated along the micropipette's moving path.

When an embryo is dispensed out from the micropipette tip, they are first positioned at the locations where the concentration is lower (i.e., similar to ES). Then the embryos are gently moved along the concentration gradient increasing direction (e.g., from right to left). After that, the embryos are washed several times by aspirating into and dispensing out of the micropipette.

Figure 9:
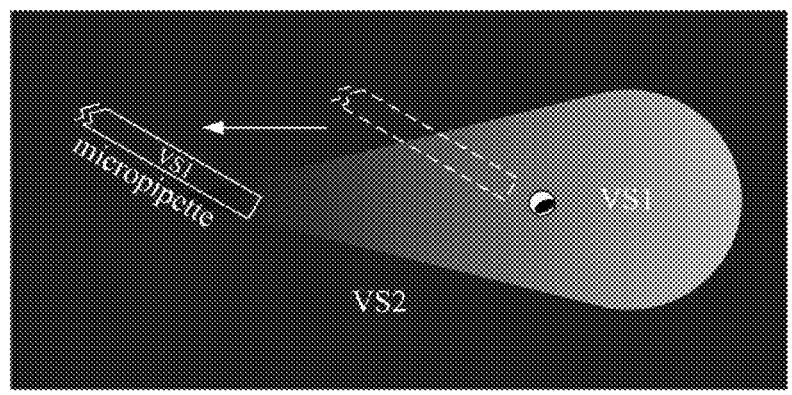
FIG. 9 Graph illustrating an example method for generating a concentration gradient when the system transfers the embryo from vitrification solution 1 (VS1) to VS2.

FIG. 9 illustrates an example method for generating a concentration gradient. VS2 often has the same solutes as VS1 but at a higher concentration. In order to generate a concentration gradient, VS1 is infused into VS2 at a constant rate while the robot moves the micropipette to the left direction at an increasing speed with a constant acceleration.

Another method to minimize osmotic shock pressure is to use a series of vitrification solutions with moderate concentration changes. However, this method involves more types of VS and more steps of embryos pick-and-place.

Removal of Excessive VS from the Vitrification Straw

Figure 10:
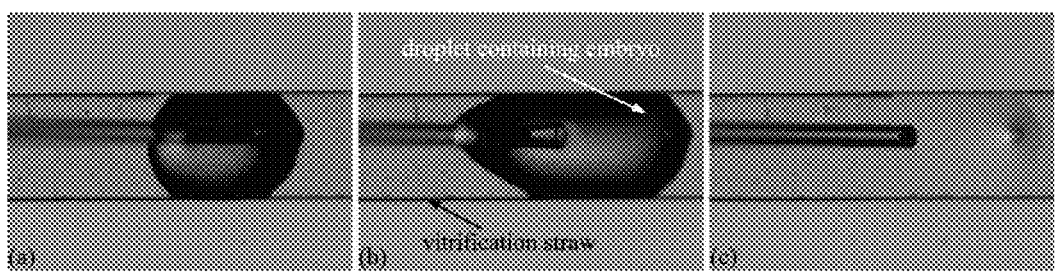
FIG. 10 are images illustrating automated removal of excessive medium after placing an embryo on the vitrification straw tip in accordance to one embodiment of the present invention. (a) A relatively large medium obtaining the embryo is deposited onto the straw surface. (b) A thin film of medium is formed on the straw surface by the robot's dragging the micropipette tip to the left. (c) Excessive medium is aspirated away automatically by applying a negative pressure. Embryo stays in initial position because of friction.

After robot 501 places a vitrified embryo onto the straw, the system removes excessive medium to achieve a high cooling rate. As shown in FIG. 10(a)(b), the system first dispenses the embryo in a relatively large volume of VS solution onto the vitrification straw. Robot 501 then moves the micropipette on the straw surface away from the initial dispensing location to form a thin VS film. The robotic system controls the motorized syringe to aspirate VS until the volume of the embryo droplets stops changing [FIG. 10(c)]. While VS medium is aspirated into the micropipette, friction force keeps the embryos in its original place.

Throughout this step, the system utilizes image processing to monitor droplet volume change and micropipette tip positions. The embryo is also detected from the straw ROI by using the methods described in the previous section "Embryo Detection/Tracking". Since the embryo is surrounded by the excessive medium, the volume of the detected object is proportional to the volume of the excessive medium. Accordingly, when the detected embryo volume stops changing, it is considered that all excessive medium has been removed from the vitrified embryo.

Vitrification Straw Sealing

The vitrification straw sealing machine is design to automatically place a plastic cap onto the straw tip in order to avoid contamination during the long-term cryopreservation. As shown is FIG. 11, the sealing machine comprises a mechanical guiding mechanism, which allows a sliding part to move towards the fixed part. The vitrification straws and plastic taps are mounted on predefined slots/positions on the sliding part and fixed part, respectively. After the straws are placed by robot 502 on the sealing machine, the system controls a motor to drive the sliding part to the fixed part until a limit switch is triggered, which completes the capping/sealing process.

Automated Liquid Nitrogen Storage System

Figure 12:
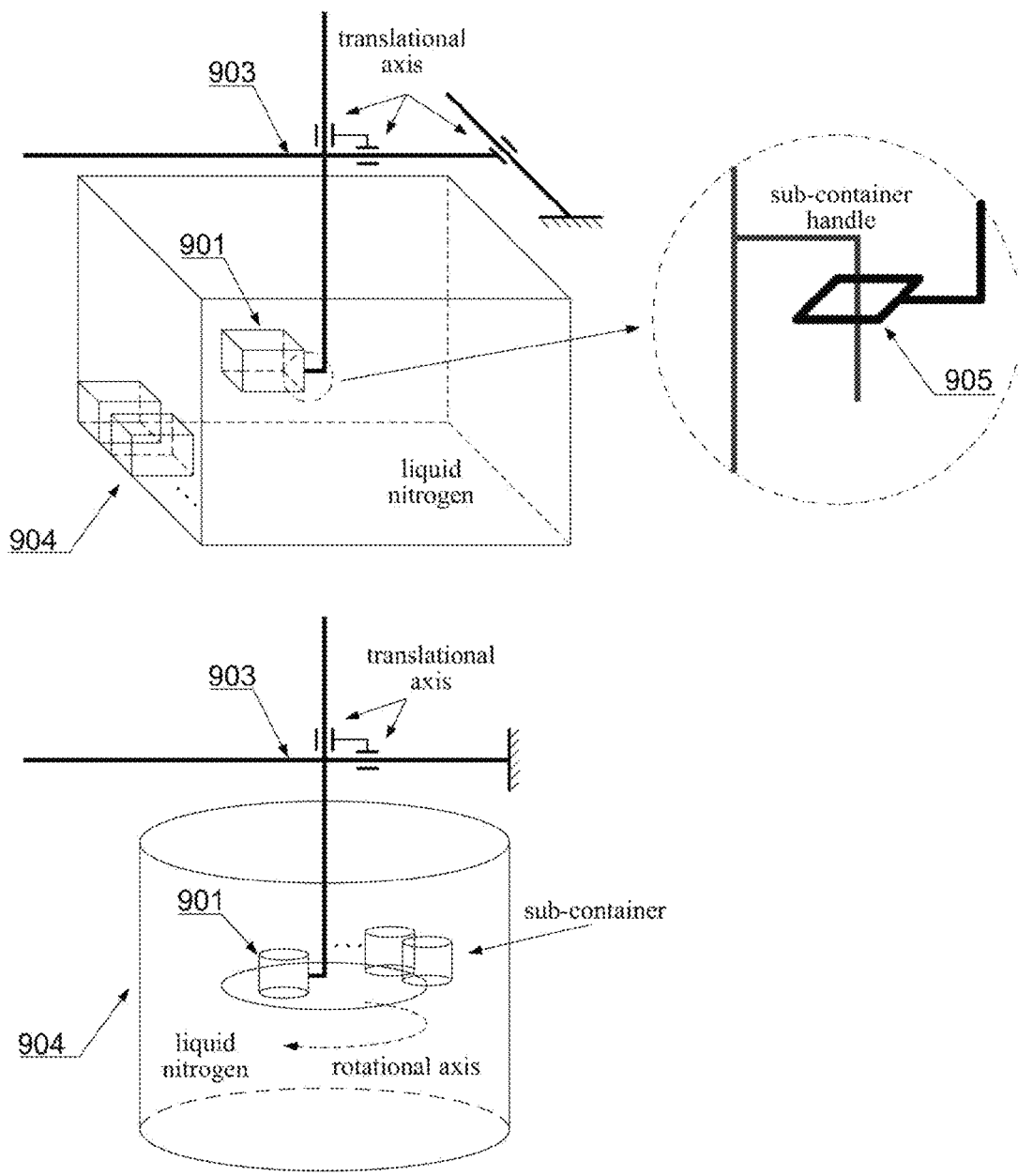
FIG. 12 is a graph illustrating an example design of an automated liquid nitrogen storage system in accordance to one embodiment of the present invention.

As part of the robotic vitrification system, an automated liquid nitrogen storage system is designed. The automated storage system comprises a liquid nitrogen tank, a built-in 3-axis transport system, and liquid nitrogen sub-containers. The three-axis transport system 903 is automated to locate a sub-container 901 and transfer it into or out of the storage tank 904 containing liquid nitrogen. As shown in FIG. 12, the transport system 903 may include three translational motion axes or two translation axes plus one rotational axis to rotate sub-containers insider the storage tank. As the end-effector of the transport system, a mechanical mating loop 905 holds the handle of the sub-container.

Figure 13:
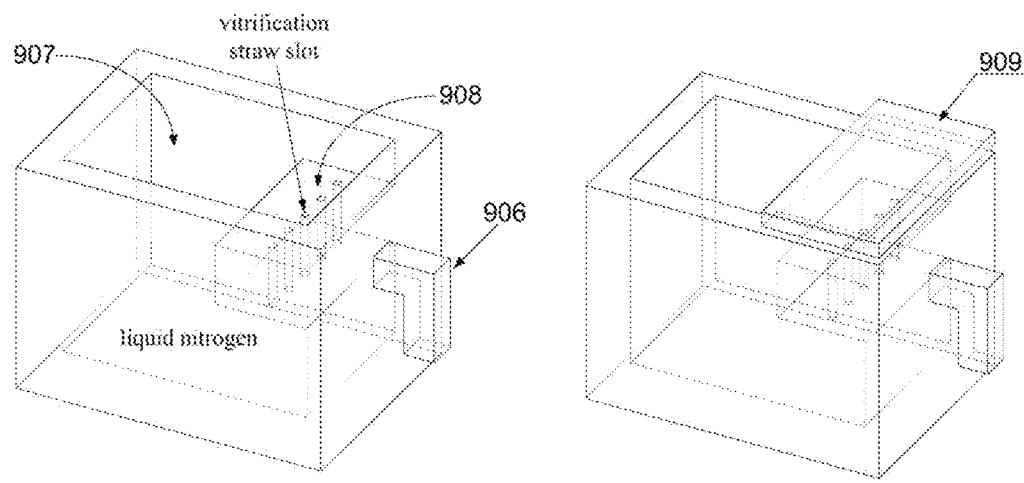
FIG. 13 illustrates an example design of a liquid nitrogen sub-container with slots for vitrified sample storage in accordance to one embodiment of the present invention: left region has open space to freeze vitrification straws, while the right region has a number of slots for storage of frozen sample. A lid can be placed on the sub-container in order to keep the vitrification straws in place.

As shown in FIG. 13, the sub-container 901 is designed as the sub-unit of the automated storage system 902 for freezing and storing vitrification straws. The sub-container 901 has a handle 906 for the end-effector of the transport system to connect to, a vitrification freezing region 907, and a storage region 908 having multiple slots for frozen straws to insert in. To prevent the vitrification straws' free motion in the storage region, the sub-container further includes a lid 909 to cover the storage region.

E. Advantages

The system of the present invention automates the implementation of well accepted vitrification protocols. Without changing well-established protocols or modifying embryo handling approach, the system of the present invention can be easily accepted in clinics.

Embryos are monitored in real time throughout the entire vitrification process, which can effectively avoid embryo loss.

The systems and methods of the present invention are fully automated including the loading and retrieving embryos (vs. manual loading in microfluidic vitrification), and detecting the embryos position in solutions (as opposed to the manual input in patient by Ru et al. in Chinese Pat. Appl. Publ. No. 202918907U).

The systems and methods of the present invention can generate a moderate concentration gradient which can minimize the osmotic pressure and further increase the cell survival rate.

The systems and methods of the present invention can automatically place vitrified embryos onto vitrifications straws and remove excessive surrounding solutions to achieve 'minimal volume', in order to achieve high cooling rates for freezing.

The systems and methods of the present invention is capable of processing multiple embryos with an optimized schedule for saving the total processing time.

The systems and methods of the present invention includes an automated sealing machine that can be used to place caps to vitrification straws, and an automated cryopreservation storage system which can eliminate human errors in embryo handing.

The oocytes, embryos and cells are exposed to the different processing solutions (i.e. washing, equilibrium, vitrification, thawing solutions) as uniformly as in the standard manual protocols.

Through the embodiments that are illustrated and described, the currently contemplated best mode of making and using the invention is described. Without further elaboration, if is believed that one of ordinary skill in the art can, based on the description presented herein, utilize the present invention to the full extent.

Although the description above contains many specificities, these should not be construed as limiting the scope of the invention, but as merely providing illustrations of some of the presently embodiments of this invention. Thus the scope of the invention should be determined by the appended claims and their legal equivalents, rather than by the examples given.

What is claimed is:

1. An automated biological material cryopreservation and thawing system comprising:
   (a) a carrier plate having (i) an area for holding unprocessed biological material, (ii) a multi-well area for holding biological material processing solutions, and (iii) a straw area for holding one or more vitrification straws;
   (b) a first robot connected to a manipulator to manipulate the biological material and the processing solutions;
   (c) a multiple degrees of freedom second robot to manipulate the vitrification straws;
   (d) a microscope and an image capturing device operatively linked to the microscope to capture images of the biological material, the manipulator and the vitrification straws;
   (e) a computer readable medium having executable instructions;
   (f) an automated vitrification straw-sealing machine and an automated cryopreservation storage device; and
   (g) a processor for executing the executable instructions of the computer readable medium; said executable instructions including instructions for automatically: (i) processing the captured images, and (ii) operatively controlling the microscope, the image capturing device, the first robot, and the second robot, and wherein the instructions for operatively controlling the second robot, include instructions to seal the vitrification straw in the vitrification straw-sealing machine, and to transfer the sealed vitrification straw into the automated cryopreservation storage device.

2. The system of claim 1, wherein the executable instructions further include instructions for automatically operatively controlling the straw-sealing machine and the automated cryopreservation storage device.

3. The system of claim 1, wherein the executable instructions further include instructions for:
   (i) when the biological material is a cell, embryo or oocyte, detecting the cell, embryo or oocyte at different development stages from the captured images;
   (ii) tracking the biological material inside the processing solutions in three dimensional space;
   (iii) monitoring the biological material's volume;
   (iv) generating a concentration gradient in the treatment solutions;
   (v) placing the biological material on the vitrification straws; and
   (vi) removing excessive treatment solution from biological material placed on the vitrification straw.

4. The system of claim 1, wherein the executable instructions further include instructions to automatically change focus and magnification of the microscope.

5. The system of claim 1, wherein said microscope includes an X-Y stage for receiving the carrier plate, the X-Y stage including an X-axis linear motion system and a Y-axis linear motion system, and wherein the executable instructions further include instructions to operatively controlling the X-Y stage.

6. The system of claim 5, wherein the microscope is operationally linked to a controller having a driver for each of said X and Y axis linear motion system.

7. The system of claim 6, wherein said X-axis linear motion system and the Y-axis linear motion system are independently controllable.

8. The system of claim 1, wherein said first and second robots have at least three degrees of freedom.

9. The system of claim 1, wherein said area for holding the biological material is integrated with a heating plate.

10. The system of claim 2, wherein said a straw sealing machine includes a preset straw loading position, a preset straw cap loading position, and a mechanical guiding mechanism to move the cap to the vitrification straw.

11. The system of claim 2, wherein said automated cryopreservation storage system includes a cryopreservation solution tank for holding the cryopreservation solution, a movable sub-container and a 3-axis transport system automated to locate and transport the sub-container.

12. The system of claim 11, wherein said movable sub-container has at least one position to hold at least one vitrification straw.

13. The system of claim 11, wherein said movable sub-container has a freezing region with an opening space for directly freezing vitrification straws.

14. The system of claim 11, wherein said movable sub-container has at least one handle for connection to the built-in transport system.

15. The system of claim 14, wherein the built-in transport system has at least one linear motion part, wherein said the linear motion part is controlled to move reciprocally to take the sub-container out of the tank, or put it into the tank.

16. The system of claim 3, wherein said computer executable instruction for detecting cell, embryo or oocyte at different development stages includes:
    image binarization to produce a binarized image, detecting potential cell targets from foreground objects in the binarized image, and fitting circles on potential cell targets.

17. The system of claim 16, wherein said detection involves automatically changing the magnification of microscope and coordinately moving X-Y stage.

18. The system of claim 17, wherein said detection starts with the detection of the cell, embryo or oocyte under lower magnification, and then X-Y stage is controlled automatically to move the detected cell, embryo or oocyte to the center of field of view.

19. The system of claim 3, wherein said computer executable instruction for tracking biological material in three-dimensional space further detects the biological material's Z position.

20. The system of claim 19, wherein said the detection of biological material's Z position involves the automated adjustment of the microscope's focal plane along the Z axis.

21. The system of claim 1, wherein said computer executable instruction for automatically placing the biological material on the vitrification straw further includes detection of the manipulator tip's contact on the vitrification straw tip.

22. The system of claim 21, wherein said detection of contact on the vitrification straw tip is based on detecting the vitrification straw tip's deflection arising from the contact of the manipulator's tip with the vitrification straw tip.

23. The system of claim 22, wherein said detection of straw tip's deflection is via motion detection.

24. The system of claim 1, wherein the manipulator is a micropipette, and the system further comprises a motorized syringe to generate pressure for micropipette aspiration or dispensing.

25. The system of claim 1, wherein the biological material is a cell, an oocyte and/or an embryo.

\* \* \* \* \*